United States Patent [19]

Wand et al.

[11] Patent Number: 5,453,218

[45] Date of Patent: Sep. 26, 1995

[54] LIQUID CRYSTAL COMPOUNDS CONTAINING CHIRAL 2-HALO-2 METHYL ALKOXY TAILS

[75] Inventors: Michael D. Wand, Boulder; Kundalika M. Moré, Denver; William N. Thurmes, Longmont, all of Colo.

[73] Assignee: Displaytech, Inc., Boulder, Colo.

[21] Appl. No.: 193,254

[22] Filed: Feb. 8, 1994

Related U.S. Application Data

[63] Continuation-in-part of Ser. No. 6,263, Jan. 19, 1993, which is a continuation-in-part of Ser. No. 164,233, Mar. 4, 1988, Pat. No. 5,051,506.

[51] Int. Cl.$^6$ .......................... C09K 19/52; C09K 19/34; C07D 239/02; C07C 43/00
[52] U.S. Cl. ........................ 252/299.01; 252/299.61; 252/299.63; 544/242; 544/336; 546/346; 548/136; 568/588; 568/647; 570/127
[58] Field of Search .................. 252/299.01, 299.61, 252/299.63, 299.64, 299.65, 299.66; 544/242, 336; 546/346; 548/136; 549/369; 568/588, 647; 570/127

[56] References Cited

U.S. PATENT DOCUMENTS 5,051,506  9/1991  Wand et al. ..................... 252/299.01

FOREIGN PATENT DOCUMENTS 2-183231  7/1990  Japan .

Primary Examiner—Shean Wu
Attorney, Agent, or Firm—Greenlee and Winner

[57] ABSTRACT

This invention provides chiral nonracemic compounds of formula

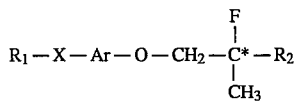

wherein * indicates a chiral carbon, $R_1$ and $R_2$, independently of one another, can be an alkyl, alkenyl or alkynyl group wherein one or more non-neighboring $CH_2$ groups can be replaced with an O, S or a silyl group $(R_A SiR_B)$ wherein $R_A$ and $R_B$, independently of one another, are alkyl or alkenyl having from one to six carbon atoms; $R_1$ having from about 3 to 20 carbon atoms, and $R_2$ having from 1 to about 18 carbon atoms; X is O, S, CO, COO, OCO, COS or a single bond where Ar is a liquid crystal core moiety having two or three aromatic rings of the formula $$-(Cyc)_n-(A)_a-Ph_1-(B)_b-Ph_2-(C)_c-(Ph_3)_m-$$

wherein $Ph_1$, $Ph_2$ and $Ph_3$, independently of one another, are selected from the group of aromatic rings:
1,4-phenyl group, 1,4-phenyl group substituted with 1 or 2 halogens, 1,4-phenyl group wherein one or two of the ring carbons are replaced with nitrogen atoms or a thiadiazole ring;

A, B and C, independently of one another, can be O, S, $CH_2O$, $OCH_2$, $CH_2S$, $SCH_2$, $CH_2OCO$, $CH_2CO_2$, $CH_2CH_2$, COO, OCO, COS, a double or triple bond; a, b and c are either 1 or 0 and a+b+c is 2 or less; Cyc is a 1,4 substituted cyclohexyl or a cyclohexenyl ring which can be further substituted with halogen atoms or cyano group or wherein one or two of the $CH_2$ groups of the ring can be replaced with an oxygen atom; and n and m, independently of one another, are 0 or 1. These compounds are useful as components of FLC compositions for use particularly in SSFLC and DHFLC devices.

46 Claims, No Drawings

LIQUID CRYSTAL COMPOUNDS CONTAINING CHIRAL 2-HALO-2 METHYL ALKOXY TAILS

RELATED APPLICATIONS

This application is a continuation-in-part of U.S. patent application Ser. No. 08/006,263, filed Jan. 19, 1993 now pending, which in turn is a continuation-in-part of U.S. Pat. No. 5,051,506, issued Sep. 29, 1991 based on application Ser. No. 164,233, filed Mar. 4, 1988. U.S. Ser. No. 006,263 and U.S. Pat. No. 5,051,506 are incorporated by reference herein in their entirety.

FIELD OF THE INVENTION

The present invention relates to compounds and liquid crystal compositions containing them useful in electro-optical and display device applications.

BACKGROUND OF THE INVENTION

Lagerwall and Clark described the surface-stabilized ferroelectric liquid crystal (SSFLC) effect and its application to electro-optic shutters and display devices (U.S. Pat. Nos. 4,367,924 and 4,563,059). SSFLC devices can display electro-optic effects with very fast (sub-microsecond) switching speeds.

Tilted smectic liquid crystal phases particularly smectic C phases composed of chiral, nonracemic molecules possess a spontaneous ferroelectric polarization, or macroscopic dipole moment, deriving from a dissymmetry in the orientation of molecular dipoles in the liquid crystal phases (Myer et al. (1975) J. Phys. (Les Ulis, Fr) 36:L-69). The ferroelectric polarization density is an intrinsic property of the material making up the phase and has a magnitude and sign for a given material under a given set of conditions.

In SSFLC cells, the FLC is aligned between transparent electrodes in the so called "bookshelf" alignment in which the smectic layers are substantially perpendicular to the electrodes and the long axis of the FLC molecules are parallel to the electrodes. In this configuration, the natural helix typically formed in the ferroelectric phase is suppressed by surface interactions in the cell. Suppression of the helix results in a bistable cell in which the optic axis of the cell can be rotated in the plane of the electrodes by $2\Theta$, where $\Theta$ is the tilt angle, by changing the sign of the applied driving voltage. Tilt angle is an intrinsic property of a FLC material. This switching of rotation of the optic axis can be employed for light modulation. Within a large range of electric field strengths, the switching speed (optical rise time) is inversely proportional to applied field strength and polarization or dipole density ($P_s$), and directly proportional to orientational viscosity. Fast switching speeds are associated with FLC phases which possess high polarization density and low orientational viscosity.

In order to suppress the helix, the SSFLC cell thickness (d) must be comparable to or smaller than the magnitude of the pitch of the helix in the ferroelectric phase. Thus, for applications in the visible in which cell thicknesses of 0.5–6 μm are most useful (assuming a birefringence of 0.15–0.3), the SSFLC natural ferroelectric phase helix pitch in the FLC should be longer than 0.5–10 μm.

Electro-optic effects in FLC cells in which the helix in the smectic C* phase is not suppressed by surface-stabilization have also been described. The distorted helix ferroelectric (DHF) effect, described for example in Ostovski et al., Advances in Liquid Crystal Research and Applications, Oxford/Budapest. (1980) page 469 and in Funfschilling and Schadt (1989) J. Appl. Phys. 66(8):3877–3882), is observed in FLCs aligned between electrode plates in which the natural helix pitch in the smectic C* (or other chiral tilted smectic ferroelectric) phase is sufficiently tight, i.e., shorter than the FLC cell thickness (d), so that the helix is not suppressed. DHFLC electro-optic devices have an FLC aligned between electrode plates. Most typically the FLC is planar aligned and in the "bookshelf" geometry. A driving voltage is applied to the electrodes to generate an electric field across the FLC layer. Unlike, SSFLC devices, the natural helix of the aligned chiral smectic phase is present in the aligned FLC material in the DHF device. The helix forms parallel to the plates and perpendicular to the smectic layers. The magnitude of the pitch of the helix is the distance along the helix axis for one full turn of the helix and the sign of the pitch (+ or −) represents the direction of twist of the helix. The term "tight" pitch, which can be a positive or negative value, is associated with shorter axial lengths for one full turn of the helix. The term "pitch" as used herein refers to the magnitude of the pitch; the terms "sign of the pitch" or "twist" refer to the direction of twist of the helix.

When the magnitude of the ferroelectric C* phase, helical pitch is comparable to the wavelength of visible light, a striped pattern appears in the device and in effect a diffraction grating is formed. If the magnitude of the pitch is less than the wavelength of light (and preferably less than ½ λ of light) light diffraction is minimized and the apparent refractive index of the FLC is the average over many director orientation of the helix. In the field-free state with zero applied electric field and with no surface stabilization, the C* helix is in its natural state. The molecular director, ñ, makes an angle, $\Theta$, with the layer normal. In the field-free (E=0) state, due to the presence of the helix, averaging occurs and the apparent optic axis of the DHFLC coincides with the helix axis.

If the voltage applied across the FLC layer is above a certain critical level $E_c$, the helix is completely unwound forming two distinct optical states, as in an SSFLC device. Application of a voltage below $E_c$ deforms the helix, generating an effective rotation of the optic axis of the DHFLC. The orientation of the optic axis of the DHFLC layer can be changed in a continuous fashion proportional to the applied electric field changing the optical anisotropy of the FLC. DHF cells display rotation of their optic axis that is dependent on the magnitude of the applied electric field and also exhibit a change in apparent birefringence ($\Delta n$) as a function of the magnitude of the applied electric field.

The maximum field-induced angle of rotation of the optic axis of the DHFLC is $\Theta$, the tilt angle of the material. A maximum field induced optic axis rotation of $2\Theta$ can be obtained by application of a ± voltage step, $\pm E_{max}$, where $E_{max}$ is the minimum voltage required to obtain a rotation of $\Theta$ and the magnitude of $E_{max}$ is less than $E_c$.

DHF-effect cells typically exhibit significantly lower apparent refractive index than SSFLC cells due to the averaging noted above. Thus, for a given desired optical retardation, DHF cells are typically thicker than comparable SSFLC cells. Birefringence for DHFLC cells typically ranges from about 0.06 to 0.13, about ½ that of SSFLC cells. DHFLC waveplates are as a consequence, typically, thicker than comparable SSFLC waveplates. High birefringence materials are thus useful in DHF applications to minimize cell thicknesses.

$E_c$ is inversely proportional to the spontaneous polarization of the FLC and the ferroelectric phase pitch, having the relationship:

$$E_c P_s \propto \left(\frac{1}{p^2}\right)$$

Thus, the higher the spontaneous polarization and longer the pitch, the lower the voltage necessary to control the effect. Response time (τ) for the DHFLC cell is a function of pitch, tilt angle and viscosity:

$$\tau \propto \gamma \frac{p^2}{\theta^2}$$

where γ is the orientational viscosity and Θ is the tilt angle. Increasing $P_s$ lowers the threshold voltage, but does not increase the speed, while tightening the pitch increases both the speed and $E_c$. By increasing both $P_s$ and decreasing p, the response speed can be significantly increased while maintaining a low threshold voltage. Also decreasing the viscosity improves the response time.

Contrast ratio of a device is defined as the ratio of the transmitted light in an ON (maximal white light transmitted through the device) and an OFF (minimal white light transmitted through the device) state. Maximum contrast is obtained when the voltage step applied across the cell rotates the optic axis by a total of 45° between OFF and ON states. Maximum transmission in the ON state can be limited if the total optic axis rotation is less than 45°, as in FLC's which have tilt angles less than 22.5°. Most often, however, contrast is limited by light leaking through in the OFF state, a function of the quality of cell alignment. Minimal OFF state transmission in both SSFLC and DHFLC requires good uniform alignment.

It is well-known in the art that improved alignment and contrast ratio in SSFLC cells can be facilitated by an FLC having a long pitch N* phase at higher temperatures to the ferroelectric tilted chiral smectic phase (see for example WO 87/06021). To facilitate alignment in SSFLCs, N* pitch should be at least equal to d, and preferably 4d or more. It is also well-known in the art for the preparation of SSFLC cells that cell alignment is further facilitated by the presence in the FLC of a smectic A phase intermediate in temperature between the chiral tilted smectic ferroelectric phase and the N* phase. SSFLC cells, as noted above, however, are also considered in the art to require relatively long pitch (typically longer than d and preferably longer than 4d) in their ferroelectric phase.

Methods analogous to those that had been successful in improving the alignment and contrast of SSFLC cells can be employed to improve the alignment and contrast in DHFLC cells. Wand et al. U.S. Ser. No. 832,414, filed Feb. 7, 1992, which is incorporated in its entirety herein by reference, reports that compositions having a tight pitch ferroelectric phase, e.g., a smectic C* phase, and a long pitch N* phase at higher temperatures can be aligned using methods such as those described in WO 87/06021. These methods combine cell surface treatment (i.e., alignment layers) with cooling of the FLC in contact with the treated surfaces of the cell plates from the nematic phase to the ferroelectric phase. Good FLC alignment and high DHFLC cell contrast result. It was also found by Wand et al. U.S. Ser. No. 832,414 that the presence of an orthogonal smectic phase, such as a smectic A phase, intermediate in temperature between the nematic and the ferroelectric phases further facilitates good alignment and the generation of high contrast DHFLC cells.

A basic requirement for application of ferroelectric liquid crystals in electro-optical devices is the availability of chemically stable liquid crystal compounds or mixtures which exhibit ferroelectric phases (chiral smectic C) over a substantial temperature range about room temperature. In some cases, the ferroelectric liquid crystal compound itself will possess an enantiotropic or monotropic ferroelectric (chiral smectic C*) liquid crystal phase. Ferroelectric liquid crystal mixtures possessing smectic C* phases with useful temperature ranges can also be obtained by admixture of chiral, nonracemic compounds, designated ferroelectric liquid crystal dopants into liquid crystal host material (which may or may not be composed of chiral molecules). Addition of the dopant can affect the ferroelectric polarization density and/or the viscosity of the C* phase and thereby affect the switching speed. Desirable FLC dopants are molecules which impart high ferroelectric polarization density to an FLC material without significantly increasing the orientational viscosity of the mixture. The components of FLC mixtures can also be adjusted to vary phase transition temperatures or to introduce desired LC phases. The components of FLC mixtures can also be adjusted to vary N* pitch and C* pitch.

Thermotropic liquid crystal molecules typically possess structures which combine a generally linear and generally rigid liquid crystal core coupled with two relatively "floppy" tails (see Demus et al. (1974) Flussige Kristalle In Tabellen, VEB Deutscher Verlag fur Grundstoffindustrie, Lebzig for a compilation of the molecular structures of LC molecules). FLC dopants typically possess rigid LC cores and at least one flexible tail. FLC materials have been prepared by the introduction of a stereocenter into one (or both) of the tails, thus introducing chirality.

In bistable SSFLC applications, large $P_s$ (spontaneous polarization density), fast rise time, low orientational viscosity, long N* pitch and long C* pitch are desirable. Large $P_s$, fast rise time, and low orientational viscosity all relate to the switching speed upon application of an optimal field. The N* and C* pitch are both manifestations of the chirality of the liquid crystal material and are intrinsic properties of FLC components. Although both are helices formed in the liquid crystal, they propagate in different directions and bring different complications to a FLC light modulator. The N* helix, in a surface stabilized FLC with planar geometry, runs perpendicular to the substrates, whereas in the same FLC, the C* helix runs parallel to the substrate. As noted above, the N* helical repeat length or pitch, measured at the N→A or N→C transition, should be more than four times the width of the cell to give preferred consistent alignment of the FLC (Uchida, T. et al. (1989) Liquid Crystals 5:1127).

In DHFLC applications large Ps, fast rise time, low orientational viscosity also are desirable and a very tight C* pitch is required. For good alignment, DHFLC materials preferably combine long N* pitch with the very tight C* pitch.

SUMMARY OF THE INVENTION

The present invention provides new classes of FLC compounds, chiral nonracemic compounds having a 2-fluoro-2-methyl alkoxyl chiral tail, which impart improved properties to LC and FLC compositions.

The present invention provides 2-fluoro-2-methyl alkoxy compounds of the general formula I:

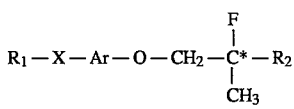

where * indicates the chiral carbon and where Ar can be any of a wide variety of LC core moieties but, in particular, can be those having two or three aromatic rings of the general formula:

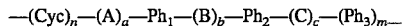

where a, b and c are either 0 or 1 and a+b+c is 2 or less; n and m, independently of one another, are 0 or 1; A, B and C, independently of one another, are selected from the group of O, S, $CH_2S$, $SCH_2$, $CH_2CH_2$, $CH_2O$, $OCH_2$, $CH_2CO_2$, $CH_2OCO$, COO, OOC, COS, a double or a triple bond; Cyc is a 1,4-cyclohexyl ring or a 1,4-cyclohexenyl ring, either of which can be further substituted with halogen atoms or cyano groups and wherein one or two non-neighboring $CH_2$ groups of the ring can be replaced with an 0 atom; the aromatic rings $Ph_1$, $Ph_2$ and $Ph_3$ independently of one another, are selected from the group 1,4-phenyl, 1,4-phenyl substituted with one or two halogen atoms, 1,4-phenyl in which one or two of the ring carbons are replaced with nitrogen atoms or a thiadiazole ring; X is selected from the group O, S, COO OOC, COS or a single bond; $R_1$ and R2 independently of one another, are selected from an alkyl, alkenyl or alkynyl group in which one or more non-neighboring $CH_2$ groups can be replaced with an O, S or an alkyl silyl group, $S_1(R_A)(R_B)$, in which $R_A$ and $R_B$, independently of one another, are small alkyl or alkene groups having from one to six carbon atoms. $R_1$ has from about three to about twenty carbon atoms and $R_2$ has from one to about eighteen carbon atoms.

The chiral tail group, generically designated R* in Tables 1–6 of exemplary cores, can have either the S or R configuration. $R_2$ can be branched or straight chain or contain a cycloalkyl portion, such as a cyclopropane ring. As defined above $R_2$ can include, among others, alkyl, alkenyl, alkynyl, ether, thioether, alkyl silyl or alkenyl silyl groups. The first atom in $R_2$, bonded to the chiral carbon, is preferably a carbon. Preferred $R_2$ are alkyl. Preferred alkenyl and alkynyl groups are monoalkenyl and monoalkynyl groups. Preferred alkyl silyl groups comprise dimethyl silyl groups $Si(CH_3)_2$. $R_2$ groups that are ethers or thioethers can also contain one or more double bonds. Preferred ether and thioether groups contain a single O and S, respectively. More preferred $R_2$ groups contain from about two to twelve carbon atoms.

In general, suitable liquid crystal cores are rigid, linear moieties. Preferred cores are those that are chemically stable and which do not impart high orientational viscosity in the liquid crystal phase. Specific cores of this invention have two or three aromatic rings and optionally contain a cyclohexane or cyclohexene ring. It has been found that 2-fluoro-2-methyl alkoxy LC compounds having three aromatic rings have generally higher polarization than those with cores having two aromatic rings.

The cyclohexane or cyclohexene ring is preferably linked at its 1 and 4 positions between $R_1X$ and —$(A)_a$—$Ph_1$. The cyclohexane or cyclohexene rings may be further substituted with halogen atoms or cyano groups and one or two non-neighboring $CH_2$ groups of the ring may be substituted with an O atom.

The cyclohexane or cyclohexene ring can be directly linked to an aromatic ring of the core or linked through a linking group, for example a $CH_2O$, $OCH_2$, $CO_2$ or OOC group. The preferred linking group is $CH_2O$. The cyclohexane or cyclohexene ring is preferably in the trans configuration. The double bond of the cyclohexene ring is preferably in the 3,4-bond adjacent to the site of $R_1X$ group substitution. The preferred cyano substitution is at the axial 1 position on the ring carbon bonded to the $R_1X$ group:

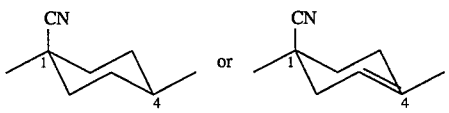

The preferred oxygen-containing cyclohexane ring is that with oxygens in place of the 3 and 5 carbons as indicated:

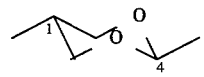

The aromatic rings of the core $Ph_1$, $Ph_2$ and Ph3 can in general be any aromatic ring, but more specifically are selected from the group 1,4-phenyl, 1,4-phenyl substituted with one or two halogens, 1,4-phenyl in which one or two ring carbons are replaced with nitrogen atoms. Nitrogen-containing aromatic $Ph_{1-3}$ include among others pyrimidinyl, pyridinyl, diazinyl, pyrazinyl and pyridizinyl rings. Preferred halogens are fluorine.

Exemplary $Ph_{1-3}$ include, but are not limited to, 1,4-substituted phenyl rings: mono- and dihalogenated rings:

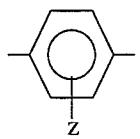

mono- and difluoro rings, including ortho, meta and ortho, meta fluorine substitution:

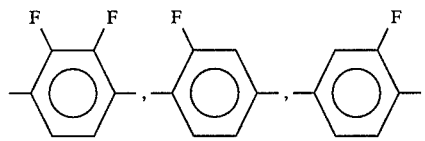

2,5-substituted pyridine rings:

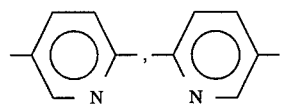

2,5-substituted pyrimidine rings:

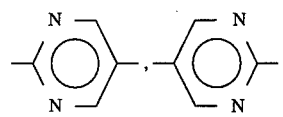

2,5-substituted pyrazine rings:

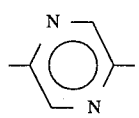

3,6-substituted pyridizine rings:

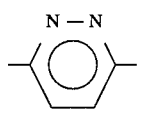

and thiadiazole rings:

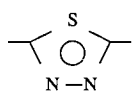

Preferred nitrogen-containing $Ph_{1-3}$ moieties are 2,5-substituted pyridine and 2,5-substituted pyrimidine rings.

Aromatic rings of the core can be directly linked to one another, preferably in a para arrangement, or by means of linking groups B and C. Compounds of this invention can optionally have one or two linking groups. When present, preferred linking groups are a triple bond or COO and OOC groups. Again the $Ph_{1-3}$ and the linking groups are preferably linked in a para arrangement to generate a generally linear core.

The tail units $R_1X$ and $R^*$, i.e. the chiral nonracemic $O-CH_2CF(CH_3)R_2$ group, are preferably linked on opposite ends of the core in a para arrangement.

The compounds of the present invention have $R_1$ which can be chiral nonracemic or achiral. $R_1$ tails include, among others, alkyl, alkenyl, alkynyl, thioether, or alkyl silyl groups having from about three to about twenty carbon atoms. $R_1$ tails can be straight-chain, branched or contain cycloalkyl portions, e.g. cyclopropane moieties. Preferred alkyl tails have from about five to twelve carbon atoms. Preferred alkenyl and alkynyl tails have one double and one triple bond, respectively. Double bonds may be cis or trans. Ether and thioether tails preferably have a single O and S atom, respectively. Ether and thioether tails may also contain one or more double bonds, not adjacent to the O or S atom respectively. The $R_A$ and $R_B$ of silyl groups can include methyl, ethyl, propyl and vinyl groups, among others. Alkyl silyl tails preferably have a dimethyl silyl group.

This invention provides LC and FLC compositions, mixtures of two or more component compounds, comprising one or more of the chiral nonracemic 2-fluoro-2-methyl alkoxy compounds of this invention.

In general, the chiral nonracemic 2-fluoro-2-methyl alkoxy compounds of this invention are useful as components of liquid crystal compositions to impart desired properties to the composition. Certain of these compounds can impart fast switching speeds to low polarization materials to form FLC useful for SSFLC or DHFLC applications. Certain of these compounds can affect the N* and/or C* pitch of FLC compositions. Certain of these compounds, for example those having N* pitch which is opposite in sign from their polarization density, can be employed to elongate N* pitch without detriment to polarization density, i.e. can function as pitch compensation agents. Certain of the compounds having N* pitch opposite in sign to C* pitch are particularly useful to obtain mixtures having short C* pitch essential for DHFLC operation in combination with long N* pitch preferred for better FLC layer alignment and improved contrast in liquid crystal devices.

DETAILED DESCRIPTION OF THE INVENTION

The chiral nonracemic 2-fluoro-2-methyl alkoxy tail of this invention can be combined with a wide variety of LC cores to provide useful components of LC or FLC compositions.

Compounds of this invention having two aromatic rings in the core include those of formulas Ia and Ib where the chiral nonracemic 2-fluoro-2-methyl alkoxy tail is indicated as $R^*$:

$$R_1-X-Ph_1-Ph_2-R^* \qquad \text{Ia/Ia'}$$

$$R_1-X-Ph_1-B-Ph_2-R^* \qquad \text{Ib/Ib'}$$

where $R_1$, X, $Ph_1$, $Ph_2$ and B are as defined above for formula I. Formulas Ia' and Ib' represent those formulas where the indicated core is reversed with respect to R, X and $R^*$. Tables 1 and 2 provide examples of the cores of Ia and Ib respectively. Compounds of formula Ia where at least one of $Ph_1$ or $Ph_2$ is a 2,5-pyridinyl or a 2,5-pyrimidyl are of particular interesting. Compounds of formula Ia include phenyl pyridines and phenyl pyrimidines and their halogenated analogs. Compounds of formula Ib include phenylbenzoates, reverse phenylbenzoates and tolanes, among others. Tolanes, where B is a triple bond, are of particular interest for applications requiring high birefringence. Thiadiazole rings are preferably linked to a 1,4-phenyl ring.

Compounds of this invention having three aromatic rings include those of formulas Ic–If:

$$R_1-X-Ph_1-Ph_2-Ph_3-R^* \qquad \text{Ic/Ic'}$$

$$R_1-X-Ph_1-B-Ph_2-Ph_3-R^* \qquad \text{Id}$$

$$R_1-X-Ph_1-Ph_2-C-Ph_3-R^* \qquad \text{Ie}$$

$$R_1-X-Ph_1-B-Ph_2-C-Ph_3-R^* \text{If/If'}$$

where $R_1$, $X_1$, $Ph_{1-3}$, B and C are as defined above for formula I. Formulas Ic' and If' represent those formulas where the core is reversed with respect to R, X and $R^*$. Compounds of formula Ic where at least one of $Ph_{1-3}$ is a 2,5-pyridinyl or 2,5-pyrimidinyl ring are of interest. Compounds of formula Ic where one of $Ph_{1-3}$ is a 2,5-pyrimidinyl are of particular interest in applications requiring FLC components having N* pitch and polarization of opposite signs. Compounds of formula Id and Ie include phenyltolanes, where B or C is a triple bond; biphenylbenzoates, where B or C is COO; phenyl (phenylbenzoates), where B or C is OOC. Phenyltolanes of formula Id and Ie are further useful in high birefringence applications. Compounds of formula If include those in which both B and C are triple bonds and in which one of B or C is COO or OOC and the other of B or C is a triple bond. Compounds of formula If having at least one triple bond are further useful in high birefringence applications. Exemplary cores of formulas Ic–If are given in Tables 3–5. Table 4 exemplifies cores of both formulas Id and Ie dependent upon the orientation of the core with respect to $R_1-X$ and $R^*$. Compounds of this invention having a cyclohexene or cyclohexane ring include those of formulas Ig and Ih:

$$R_1-X-Cyc-CH_2-O-Ph_1-Ph_2-R^* \qquad \text{Ig}$$

$$R_1—X—Cyc—Ph_1—Ph_2—R* \qquad Ih$$

where $R_1$, X, Cyc, $Ph_{1-2}$ are as defined for formula I above. Cyc includes both a trans-cyclohexyl (c-$C_6H_{10}$) or a trans-cyclohexenyl (c-$C_6H_8$), among others. In particular, Cyc can be:

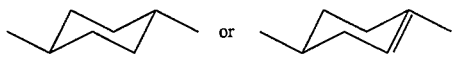

Cyc also includes cyclohexane and cyclohexene rings substituted with halogens or cyano groups. Axial substitution is preferred. Compounds of formulas Ig and Ih with a cyclohexyl group having a cyano (CN) group at the axial orientation at position 1 (i.e. where the ring is linked to $R_1$—X): cyano are further useful in applications needing negative dielectric anisotropy. Compounds of formula Ih having the oxygen containing six membered ring:

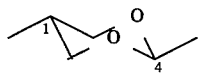

are also particularly useful in LC and FLC applications.

Compounds of formula Ig in which one of $Ph_1$ or $Ph_2$ is a 2,5-pyrimidinyl or a 2,5-pyridinyl are of interest for LC and FLC applications. Those compounds in which one of $Ph_1$ or $Ph_2$ is a 2,5-pyrimidinyl are of particular interest for such applications. Table 6 provides exemplary cores of formulas Ig and Ih.

In addition to LC cores containing two and three aromatic rings that have been detailed above, the 2-fluoro-2 methyl alkoxy tail of this invention can be combined with LC cores containing one or more than three aromatic rings. Useful core size is generally limited by limited mixing properties and increasing viscosity as the number of rings increases. Further, LC cores having only cyclohexane or cyclohexene rings or derivatives thereof, can also be combined with the 2-fluoro-2-methyl alkoxy tail to give FLC compounds. Cores having two or three cyclohexane or cyclohexene rings are typically the more useful. Dopants having cores containing only cyclohexane or cyclohexene rings tend to depress the A→C* phase transition which may be undesirable for a particular SSFLC or DHF application. However, such materials can be useful in electroclinic application or if a room temperature C* phase is present, in low birefringence SSFLC and DHF applications.

The chiral nonracemic 2-fluoro-2-methyl alkoxy compounds of this invention can be synthesized employing methods described herein in the examples, by methods well-known in the art or by routine adaptation of these methods. Starting materials for synthesis of the compounds of this invention including compounds of formulas Ia-Ih are readily available from commercial sources or by routine synthesis.

An important feature of this invention is the finding that many chiral nonracemic 2-fluoro-2 methyl alkoxy compounds having LC cores induce N* pitch and C* pitch opposite in sign when mixed with smectic C* hosts. Such compounds can be employed in DHFLC mixtures in combination with other dopants to induce long N* pitch in combination with very short C* pitch. Combination of a dopant which induces a positive N* pitch and a negative C* pitch with a compound or composition having a negative N* pitch and negative C* pitch will result in a mixture having a longer N* pitch than either of the individual components and a negative C* pitch intermediate between the C* pitch of the individual components.

Another important feature of this invention is the finding that many of the chiral nonracemic 2-fluoro-2 methyl alkoxy compounds having LC cores induce N* pitch opposite in sign to the induced polarization when mixed with smectic C hosts. Such compounds are generally useful to produce FLC compositions having long N* pitch and high polarization. Such compounds can be combined with FLC dopants which induce N* pitch and polarization having the same sign. Resultant combination will have N* pitch longer than and polarization higher than that induced by either of the individual dopants.

Tables 10 and 11 compare N* and C* pitch and polarization induced in mixtures with certain 2-fluoro-2-methyl alkoxy FLC compounds of this invention with those induced by FLC compounds having 2-fluoro alkoxy or 2,3-difluoro alkoxy tails. Compounds having three aromatic ring cores are listed in Table 10, while those having two aromatic ring cores are listed in Table 11. All of the 2-fluoro-2-methyl compounds listed in Table 10 induce N* pitch opposite in sign to the induced polarization. In contrast, structurally similar compounds having 2-fluoro alkoxy or 2,3-difluoro alkoxy tails induce N* pitch the same sign as the induced polarization. Similarly, all of the 2-fluoro-2-methyl compounds of Table 10, except MDW 652 (having a pyridine ring in the core), induce N* pitch and C* pitch of opposite sign. Comparable 2-fluoroalkoxy and 2,3-difluoroalkoxy compounds induce N* pitch and C* pitch of the same sign.

Thus 2-fluoro-2 methyl alkoxy compounds of this invention, particularly those having three aromatic ring cores are useful in SSFLC compositions and DHFLC compositions to adjust N* and C pitch. Certain of the compounds of this invention can function as pitch compensation agents, as are known in the art.

As has been detailed in U.S. Ser. No. 08/006,263 and U.S. Ser. No. 07/832,414, N* and C* induction capabilities of chiral nonracemic FLC compounds can be assessed by determining their helical twisting power (HTP), which is the inverse of the induced pitch of a mixture by the chiral nonracemic compound in a given achiral host, extrapolated to 100% concentration of that compound, i.e. HTP=(pitch× w/w %/100)$^{-1}$. This equation can be employed to calculate HTP of any of the compounds of Tables 10 or 11 where pitch data is available.

Hosts for the FLC compositions of this invention exhibit a tilted smectic phase, typically smectic C phase and preferably a nematic phase at higher temperatures. Hosts can be racemic (achiral) or chiral nonracemic. Chiral nonracemic host compositions will exhibit a ferroelectric smectic phase, e.g. a smectic C* phase. Preferred hosts have a smectic C phase at useful device operating temperatures, e.g. about 10° C. to about 80° C. More preferred hosts have an orthogonal smectic phase, for example a smectic A phase, intermediate in temperature between the smectic C and nematic phases. A dopant suitable for use with a particular host must mix with, i.e. be soluble in that host.

FLC mixtures of this invention will typically comprise from about 5% to about 50% by weight of one or a mixture of one or more of the chiral nonracemic 2-fluoro-2 methyl alkoxy compounds of formula I. Due to mixing incompatibilities and other factors well appreciated in the art, not all hosts can be combined with all FLC dopants. Selection of suitable combinations of hosts with dopants can be routinely made in view of the structures of the components and/or by routine mixing experiments.

Preferred FLC compositions for use in SSFLC applications have a suitable smectic C phase host which also exhibits a nematic phase and comprise one or more of the chiral nonracemic compounds of formula I such that the C* pitch of the mixture is equal to or greater than about d and the N* pitch of the mixture is equal to or greater than about 4 d (where d is desired layer thickness) at about 2° C. above the N* transition point. More preferred SSFLC compositions exhibit N* pitch equal to or greater than about 8 d at about 2° C. above the N* transition point while exhibiting C* pitch equal to or greater than about d.

Preferred FLC compositions for use in DHF applications have a suitable smectic C phase host and comprise one or more of the chiral nonracemic compounds of formula I such that the N* pitch of the mixture is equal to or greater than about 4 d at about 2° C. above the N* transition point and C* pitch is equal to or less than about ⅕ d. More preferred DHFLC compositions exhibit C* pitch equal to or less than about ⅒ d while retaining N* pitch greater than about 4 d.

Those of ordinary skill in the art will appreciate that variations of the methods, techniques and procedures specifically described herein can be employed to make and use the chiral nonracemic compounds and LC and FLC compositions of this invention. Various combinations of the compounds of this invention with each other and art-known LC and FLC dopants and art-known host compounds can be made to achieve useful LC and FLC compositions. All such variations and combinations are within the scope of this invention.

EXAMPLES

Example 1

Preparation of 2-(4'-Octyloxyphenyl)-5-[2S-fluoro-2-methylheptyloxyl]-2-pyrimidine This example illustrates the synthesis of chiral nonracemic 2-fluoro-2-methylalkoxy ethers by coupling a fluoromethylalkoxy tosylate with an aromatic phenol liquid crystal core.

4-n-Octyloxycyanobenzene (1)

To a solution of cyanophenol (25 g) and potassium carbonate (50 g) in 2-butanone (320 ml) was added bromooctane (61 ml) at room temperature. The stirred mixture was heated under reflux until TLC revealed complete reaction, i.e. about 48 hr. The mixture was filtered, after which the solvent and excess alkyl bromide were removed in vacuo to give a colorless liquid.

4-n-Octyloxybenzamidine hydrochloride (2)

A solution of 1(48 g) in anhydrous methanol (60 ml) and benzene (60ml) was cooled to 0° C. and anhydrous hydrogen chloride was bubbled through until the solution was saturated (ca. 15 g). The reaction mixture was stirred for 1 hr at 0° C. and then placed at 4° C. until TLC revealed complete reaction, i.e. about 48 hr. The reaction mixture was then poured into ether (300 ml) and filtered. The resultant white solid filtrant was washed with ether (50 ml) and dried in a vacuum desiccator.

The dried filtrant was dissolved in anhydrous ethanol (250 ml), and the resultant solution was cooled to 0° C. A chilled solution of ammonia in anhydrous ethanol (6M, 35 ml) was added to the cooled solution, and the resultant reaction mixture was stirred for 1 hr at 0° C. It was then allowed to stand at 4° C. for 48 hrs. The reaction mixture was then poured into ether (750 ml) and filtered. The resultant white solid filtrant, the benzamidine hydrochloride 2 was washed with ether (100 ml) and dried in a vacuum desiccator.

4'-Octyloxyphenyl-4-ethoxy-2-pyrimidine (3)

To a solution of 2 (5 g) in pyridine (80 ml) was added 1-dimethylamino-3-dimethylimino-2-ethoxypropene perchlorate (5.7 g), which was prepared according to Arnold (1973), Coll. Czech. Chem. Comm. 38: 1168. The solution was stirred at reflux for 16 hr, after which it was poured into a hydrochloric acid solution (1M, 200 ml) and extracted with three portions of ethyl acetate. The combined organic extracts were washed with brine and dried over sodium sulfate 16 hr, after which it was poured into a hydrochloric acid solution (1M, 30 ml) and extracted with three portions of ethyl acetate. The combined organic extracts were washed with brine and dried over sodium sulfate. The solvent was removed in vacuo to give 3 as a white powder.

2-(4'-Octyloxyphenyl) -5-hydroxypyrimidine (4)

Sodium hydroxide (4.2 g) was added to a solution of 3 (5.5 g) in diethylene glycol (55 ml). The resulting mixture was heated to 200° C. under nitrogen and stirred at this temperature for 8 hr. The mixture was then poured into glacial acetic acid (70 ml) yielding a white precipitate. The precipitate 4 was filtered, washed with 10 ml acetic acid and 15 ml water, then dried in a vacuum desiccator.

The exemplified method can be employed for the synthesis of two and three ring core precursors having a 2,5 pyrimidine ring adjacent to the intended site of coupling to the chiral tail. This method is readily adapted to the synthesis of two ring core precursors having pyrimidine rings. This method, for example, can be employed to generate 2,5 pyrimidine containing compounds of formula I where $R_1$ is an alkyl, alkenyl, alkynyl alkoxy, ether, thioether or alkyl silyl group. In general core precursors $R_1$—Ar—OH of this invention are commercially available, can be readily synthesized employing techniques well-known in the art or can be synthesized by routine adaptation of such well-known techniques. For example, U.S. Ser. No. 006,263 provides methods for synthesis of halogenated core precursors. Methods therein can also be employed to synthesize non halogenated cores such as phenylbenzoate and reverse phenylbenzoates.

As a further example, U.S. Ser. No. 763,134 provides methods of synthesis of two and three ring cores containing pyrimidine or pyridine rings. Compounds having thiadiazole core can be synthesized by well-known methods such as those described in EP application 89105489.2 or by routine adaptation of such methods.

Precursors for tolane cores (—Ph—C≡C—Ph)—, halogenated tolane cores and tolane-like cores in which Ph is a nitrogen-containing aromatic ring, such as a pyridine, pyrimidine, pyridizine or diazine ring can be synthesized by methods now well-known in the art or by routine adaptation of such methods. Examples of synthesis of such tolane cores are given in U.S. Ser. No. 784,263 filed Oct. 29, 1991.

Cores including cyclohexyl and cyclohexenyl rings can be synthesized by methods well-known in the art or by routine adaptation of such methods. For example, methods provided in WO 87/05105, DE 3906040 and U.S. Pat. No. 5,271,864 can be employed or readily adapted to synthesize compounds of the present invention.

Cyano substituted cyclohexane or cyclohexene containing cores can be synthesized by methods well-known in the art or by routine adaptation of such methods. For example, methods in WO 86/06373 can be employed.

Example 2

Exemplary preparation of 2-fluoro-2-methyl tail precursor 2S-fluoro-2-methylheptyl toluenesulfonate (6)

To a cooled (0° C.) solution of 2 R-methyl-1,2-epoxy heptane, 5, (where R is $C_4H_9$) (645 mg) in 20 ml of ethyl ether, 0.7 ml HF (iPr)$_2$NH and 0.36 ml water was added. A balloon filled with 200 ml SiF$_4$ was attached to the reaction flask. After stirring for 2 hours, the reaction mixture was quenched with 50 ml 5% aq. KF and extracted with ethyl ether. The organic layers were washed sequentially with saturated NaHCO$_3$ and brine and thereafter dried with anhydrous NaSO$_4$. The solvent was removed in vacuo and the residue disolved in anhydrous THF (10 ml). Toluenesulfonyl chloride (TsCl, 1.05 g, 1.1 eq.) and pyridine (0.9 ml) were then added to the THF solution. The reaction was stirred 1 hr at 0° C. then allowed to stand at −20° C until TLC showed the reaction to be complete, i.e. about 24 hr. A small amount of water (ca. 200 µl) was then added to the reaction mixture to hydrolyze excess toluenesulfonyl chloride. The solution was stirred at room temperature for about another 2 hr and then poured into water. The resultant mixture was extracted three times with ethyl acetate. The combined organic extracts were washed with brine and dried over sodium sulfate and potassium carbonate. Solvent was removed in vacuo and the resultant product 6 was purified by flash chromatography using 15% ethyl acetate in hexanes as the eluent.

Various starting materials 5 where R is an alkyl, alkenyl, alkynyl, ether, thioether or alkyl silyl group, are readily available from commercial sources, from synthesis using well-known methods or from routine adaptation of well-known methods.

Dialkyl silyl groups can be introduced into R$_1$ and R$_2$ tails of the compounds of this invention employing known methods, for example as described in EP application 355,008, published Feb. 21, 1990, or by routine adaptation of such methods.

Example 3

Exemplary coupling of LC core to 2-fluoro-2-methyl alkoxy tail
2-(4'-Octyloxyphenyl)-5-[(2S-fluoro-2-methylheptoxy]-pyrimidine (7)

Dimethylformamide (5 ml) was added to a mixture of 4 (245 mg), 2S-fluoro-2-methylheptyl-1-tosylate (6), (468 mg, 2 eq.), and cesium carbonate (532 mg, 2 eq.) in a dry flask. The solution was stirred for 18 hr at 120° C., poured into aqueous hydrochloric acid (1M, 15 ml) and extracted three times with a 1:1 mixture of ethyl acetate and hexane. The combined organic extracts were washed with brine and dried over sodium sulfate and potassium carbonate. Solvent was removed in vacuo and the residue purified by flash chromatography using 1:4 ethyl acetate:hexane as the eluent to give 242 mg (77%) of 7. The product 7 was recrystallized from acetonitrile to give a white solid.

The chiral nonracemic 2-fluoro-2-methyl alkoxy tail can be coupled with appropriate LC core precursors by methods exemplified herein, by methods well-known in the art or by routine adaptation of such methods.

Example 4

Properties of Exemplary chiral nonracemic 2-fluoro-2-methylalkoxy compounds

Table 7 provides an exemplary list of chiral non-racemic 2-fluoro-2-methyl alkoxy compounds of this invention with mesomorphic properties given. Temperatures listed in Table 7 are in degrees Centigrade. The compounds listed have the S configuration in the chiral tail. Enantiomers of the compounds of Table 7, having the R configuration in the chiral tail will have mesomorphic properties identical to their corresponding S enantiomer. Signs of pitch and polarization will be reversed between enantiomers.

Example 5

LC mixtures comprising chiral nonracemic 2-fluoro-2-methyl alkoxy compounds

Table 8 provides polarization rise time and tilt angle data for 10% (w/w) mixtures of various chiral nonracemic compounds of this invention with a liquid crystal host MX6111. The composition of MX6111 is given in Table 9.

Optional rise time was measured by standard techniques in response to a driving voltage of 5 V/µm. Polarization densities (P) are given in nC/cm$^2$ and the magnitude of P was measured by standard techniques by integration of the dynamic current response on reversing the applied electric field, as described in Martinat-Lagarde (1976) *J. Phys.*37, C-3, p.129 and Martinat-Lagarde (1977) *J. Phys. Lett.* 38, L-17. Tilt angle was measured by standard techniques.

Tables 10 and 11 provide additional exemplary data for mixtures of chiral nonracemic compounds of this invention. N* and C* pitch and polarization are given.

Tables 10 and 11 also provide a comparison of N* and C* pitch and polarization among FLC compounds having chiral nonracemic 2-fluoro-2 methyl alkoxy, 2-fluoroalkoxy and 2,3-difluoroalkoxy tails.

Pitch measurements were performed using standard methods: the Cano wedge technique or by selective reflectance as described, for example, in R. Cano (1967) *Bull. Soc.* France Mineral Crysallog. XC 333 and K. Kondo et al. (1982) Jm. J. App. Phys. 21:224. N* and ferroelectric pitch can in general be measured by any method known to the art. The Cano wedge method can be employed to measure either ferroelectric (i.e., smectic C°) or N* pitch in samples having pitch longer than about 0.5 to 0.6 µm. See: R. Cano (1967) supra; P. Kassubek and G. Merer (1969) *Mol. Cryst. Liq. Cryst.* 75:249–286. Selective reflectance measurements of thick (about 400mm) homeotropically aligned cells are typically employed to measure pitch of magnitude less than about 0.5 µm. See K. Kondo (1982) supra.

Ferroelectric and N* pitch vary as a function of temperature. Typically, ferroelectric pitch tends to decrease with decreasing temperature and N* pitch tends toward infinity at the transition point between the N* phase and the lower temperature smectic phase. Often N* pitch decreases very rapidly within a few tenths of a degree above the N* transition point. Nematic phase pitch compensation agents, such as those of this invention, are employed to lengthen N* pitch at temperatures above the transition point. N* pitch as a characteristic of chiral nonracemic LC and FLC dopants is measured at about 1°–2° C. above the transition point. Ferroelectric pitch, i.e., smectic C* pitch, as a characteristic of such dopants is measured when the mixture is in the ferroelectric phase, typically in the smectic C* phase, at a temperature in the range from about 10° C. to about 80° C. for mixtures useful in device applications. If possible, C* pitch is measured at about room temperature.

TABLE 1

EXEMPLARY CORES
R$_1$-X-Ph$_1$-Ph$_2$-R*    Ia
R$_1$-X-Ph$_2$-Ph$_1$-R*    Ia'

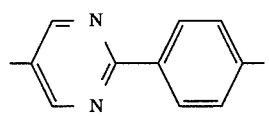

Ia1/Ia'1

TABLE 1-continued

EXEMPLARY CORES
$R_1\text{-}X\text{-}Ph_1\text{-}Ph_2\text{-}R^*$  Ia
$R_1\text{-}X\text{-}Ph_2\text{-}Ph_1\text{-}R^*$  Ia'

| Structure | Label |
|---|---|
| pyrimidine-phenyl | Ia2/Ia'2 |
| pyridine-phenyl | Ia3/Ia'3 |
| pyridine-phenyl | Ia4/Ia'4 |
| pyrazine-phenyl | Ia5/Ia'5 |
| N=N diazo-phenyl | Ia6/Ia'6 |
| phenyl-pyrimidine | Ia7/Ia'7 |
| difluorophenyl-pyrimidine | Ia8/Ia'8 |
| difluorophenyl-pyrimidine | Ia9/Ia'9 |
| difluorophenyl-pyrazine | Ia10/Ia'10 |
| difluorophenyl-pyridazine | Ia11/Ia'11 |
| difluorophenyl-pyridine | Ia12/Ia'12 |
| fluorophenyl-pyrimidine | Ia13/Ia'13 |
| fluorophenyl-pyrimidine | Ia14/Ia'14 |
| fluorophenyl-pyrazine | Ia15/Ia'15 |
| fluorophenyl-diazo | Ia16/Ia'16 |
| fluorophenyl-pyridine | Ia17/Ia'17 |
| fluorophenyl-pyridine | Ia18/Ia'18 |
| pyrimidine-fluorophenyl | Ia19/Ia'19 |
| fluoropyridine-phenyl | Ia20/Ia'20 |
| phenyl-fluoropyridine | Ia21/Ia'21 |
| phenyl-thiadiazole | Ia22/Ia'22 |

TABLE 1-continued

EXEMPLARY CORES
R₁-X-Ph₁-Ph₂-R*  la
R₁-X-Ph₂-Ph₁-R*  la'

| Structure | Label |
|---|---|
| difluorophenyl-pyridine | la23/la'23 |
| pyrimidine-difluorophenyl-R* | la24/la'24 |

TABLE 2

EXEMPLARY CORES
R₁-X-PH₁-B-Ph₂-R*  lb
R₁-X-PH₂-B-Ph₁-R*  lb'

| Structure | Label |
|---|---|
| phenyl-C≡C-phenyl | lb1 |
| phenyl(Z)-C≡C-phenyl | lb2/lb'2 |
| pyrimidine-C≡C-phenyl | lb3/lb'3 |
| phenyl-B-phenyl | lb4/lb'4 |
| phenyl(Z)-B-phenyl | lb5/lb'5 |
| pyridine-C≡C-phenyl | lb6/lb'6 |
| phenyl(Z)-C≡C-pyridine | lb7/lb'7 |
| pyrimidine-C≡C-phenyl(Z) | lb8/lb'8 |

TABLE 2-continued

EXEMPLARY CORES
R₁-X-PH₁-B-Ph₂-R*  lb
R₁-X-PH₂-B-Ph₁-R*  lb'

| Structure | Label |
|---|---|
| pyrimidine-B-phenyl | lb9/lb'9 |
| pyridine-B-phenyl | lb10/lb'10 |

B is COO or OOC and Z represents either an ortho or meta halogen or both; preferred halogens are fluorines.

TABLE 3

EXEMPLARY CORES
R₁-X-Ph₁-Ph₂-Ph₃-R*  lc
R₁-X-Ph₃-Ph₂-Ph₁-R*  lc'

| Structure | Label |
|---|---|
| phenyl-phenyl-phenyl | lc1 |
| phenyl-phenyl-phenyl(Z) | lc2/lc'2 |
| phenyl-phenyl(Z)-phenyl | lc3/lc'3 |
| phenyl-phenyl-pyrimidine | lc4/lc'4 |
| pyrimidine-phenyl-phenyl variant | lc5/lc'5 |
| pyrimidine-phenyl-phenyl(Z) | lc6/lc'6 |
| pyrimidine-phenyl(Z)-phenyl | lc7/lc'7 |
| pyrimidine-phenyl-phenyl | lc8/lc'8 |

TABLE 3-continued

EXEMPLARY CORES
R₁-X-Ph₁-Ph₂-Ph₃-R*  1c
R₁-X-Ph₃-Ph₂-Ph₁-R*  1c'

[Structure lc9/lc'9]
[Structure lc10/lc'10]
[Structure lc11/lc'11]
[Structure lc12/lc'12]
[Structure lc13/lc'13]
[Structure lc14/lc'14]
[Structure lc15/lc'15]
[Structure lc16/lc'16]
[Structure lc17/lc'17]
[Structure lc18/lc'18]
[Structure lc19/lc'19]
[Structure lc20/lc'20]
[Structure lc21/lc'21]

Z represents an ortho or meta halogen or both; preferred halogens are fluorines.

TABLE 4

EXEMPLARY CORES OF FORMULAS Id and Ie

[Structure ld1/le1]
[Structure ld2/le2]
[Structure ld3/le3]
[Structure ld4/le4]
[Structure ld5/le5]
[Structure ld6/le6]
[Structure ld7/le7]

TABLE 4-continued

EXEMPLARY CORES OF FORMULAS Id and Ie

| Structure | Label |
|---|---|
| (phenyl-OCO-phenyl-phenyl-Z) | Id8/Ie8 |
| (phenyl-C≡C-phenyl-phenyl) | Id9/Ie9 |
| (phenyl(Z)-C≡C-phenyl-phenyl) | Id10/Ie10 |
| (phenyl-C≡C-phenyl(Z)-phenyl) | Id11/Ie11 |
| (phenyl-C≡C-phenyl-phenyl(Z)) | Id12/Ie12 |
| (phenyl-C≡C-pyrimidine-phenyl) | Id13/Ie13 |
| (phenyl(Z)-C≡C-pyrimidine-phenyl) | Id14/Ie14 |
| (phenyl-C≡C-pyrimidine-phenyl(Z)) | Id15/Ie15 |
| (pyrimidine-C≡C-phenyl-phenyl) | Id16/Ie16 |
| (pyrimidine-C≡C-phenyl(Z)-phenyl) | Id17/Ie17 |
| (pyrimidine-C≡C-phenyl-phenyl(Z)) | Id18/Ie18 |
| (phenyl-C≡C-phenyl-pyrimidine) | Id19/Ie19 |
| (phenyl-C≡C-phenyl(Z)-pyrimidine) | Id20/Ie20 |
| (phenyl(Z)-C≡C-phenyl-pyrimidine) | Id21/Ie21 |
| (phenyl-C≡C-pyridine-phenyl) | Id22/Ie22 |
| (phenyl(Z)-C≡C-pyridine-phenyl) | Id23/Ie23 |
| (phenyl-C≡C-pyridine-phenyl(Z)) | Id24/Ie24 |
| (phenyl-C≡C-phenyl-pyridine) | Id25/Ie25 |
| (phenyl(Z)-C≡C-phenyl-pyridine) | Id26/Ie26 |
| (phenyl-C≡C-phenyl(Z)-pyridine) | Id27/Ie27 |
| (pyridine-C≡C-phenyl-phenyl) | Id28/Ie28 |
| (pyridine-C≡C-phenyl(Z)-phenyl) | Id29/Ie29 |

TABLE 4-continued

EXEMPLARY CORES OF FORMULAS Id and Ie

| Structure | Label |
|---|---|
| pyridine–C≡C–phenyl–phenyl with Z | Id30/Ie30 |
| phenyl(Z)–C≡C–phenyl(Z)–phenyl | Id31/Ie31 |
| phenyl–C≡C–phenyl(Z)–phenyl(Z) | Id32/Ie32 |
| phenyl(Z)–C≡C–phenyl(Z)–phenyl | Id33/Ie33 |
| phenyl(Z)–C≡C–phenyl(Z)–phenyl(Z) | Id34/Ie34 |

Z represents ortho or meta halogen substitution or both on the indicated ring; preferred haolgens are fluorine. COres of formula Id are reversed from those of formula Ie with respect to substituents $R_1$-X and R*:
Id = $R_1$-X-Core-R*
Ie = $R_1$-X-Core-R*
for Cores listed above.

TABLE 5

EXEMPLARY CORES OF FORMULA If
$R_1 - X - Ph_1 - B - Ph_2 - C - Ph_3 - R^*$ If

| Structure | Label |
|---|---|
| phenyl–C≡C–phenyl–C≡C–phenyl | If1/If'1 |
| phenyl(Z)–C≡C–phenyl–C≡C–phenyl | If2/If'2 |
| phenyl(Z)–C≡C–phenyl(Z)–C≡C–phenyl(Z) | If3/If'3 |
| pyrimidine–C≡C–phenyl–C≡C–phenyl | If4/If'4 |
| phenyl–C≡C–pyrimidine–C≡C–phenyl | If5/If'5 |
| pyridine–C≡C–phenyl–C≡C–phenyl | If6/If'6 |
| phenyl–C≡C–pyrimidine–C≡C–phenyl(Z) | If8/If'8 |
| phenyl(Z)–C≡C–pyridine–C≡C–phenyl | If9/If'9 |
| phenyl–$CO_2$–phenyl–C≡C–phenyl | If10/If'10 |
| phenyl–$CO_2$–phenyl–C≡C–phenyl(Z) | If11/If'11 |
| phenyl–$CO_2$–pyrimidine–C≡C–phenyl | If12/If'12 |
| phenyl–$CO_2$–pyridine–C≡C–phenyl | If13/If'13 |
| phenyl(Z)–$CO_2$–pyrimidine–C≡C–phenyl | If14/If'14 |
| phenyl(Z)–$CO_2$–pyridine–C≡C–phenyl | If15/If'15 |

TABLE 6

EXEMPLARY CORES OF FORMULAS Ig and Ih
$R_1X—Cyc—(A)_a—Ph_1—Ph_2——R^*$
$R_1X—Cyc—Ph_1—Ph_2—R^*$ Ih
$R_1X—Cyc—CH_2O—Ph_1——Ph_2—R^*$ Ig

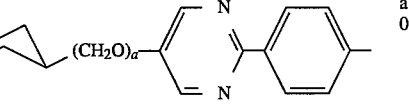

TABLE 7

| ID# | Structure | Mesomorphic Properties |
|---|---|---|
| MDW656 | 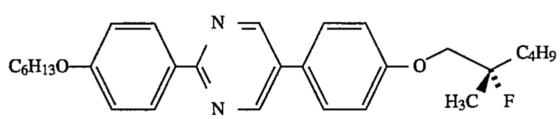 | $I \xrightarrow{157} C^* \xrightarrow[102]{88} B \xrightarrow{75} X$ |
| MDW658 | 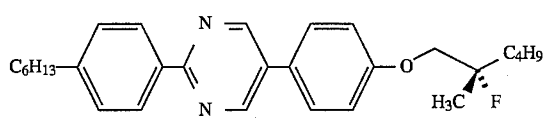 | $I \xrightarrow{127} C^* \xrightarrow[118]{118} B \xrightarrow[106]{50} X$ |
| MDW659 | 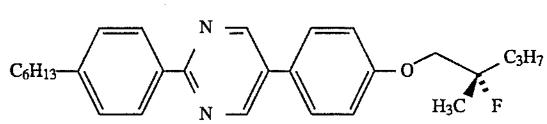 | $I \xrightarrow{130} C^* \xrightarrow[120]{120} B \xrightarrow[119]{35} X$ |
| MDW663 | 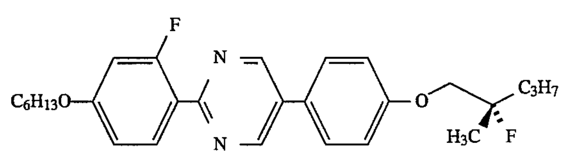 | $I \xrightarrow{108} N \xrightarrow{96} C^* \xrightarrow[105]{95} X$ |
| MDW665 | 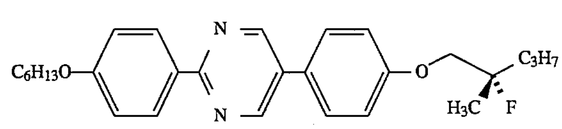 | $I \xrightarrow{125} C^* \xrightarrow[107]{97} B \xrightarrow[100]{85} X$ |

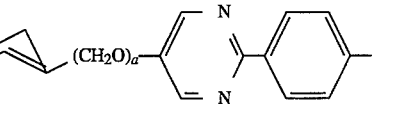
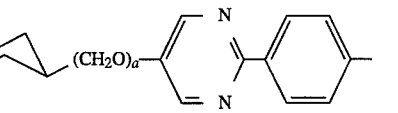
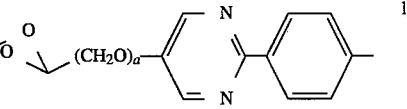
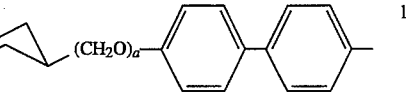
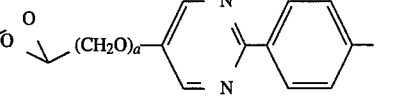

TABLE 7-continued

| ID# | Structure | Mesomorphic Properties |
|---|---|---|
| MDW666 | (structure) | I ⇌ 109/107 X |
| MDW624 | (structure) | I ⇌ 155 C* ⇌ 85/102 X |
| MDW607 | (structure) | I ⇌ 128 C* ⇌ 120/120 X |
| MDW628 | (structure) | I ⇌ 99 C* ⇌ 98/107 X |
| MDW759 | (structure) | I ⇌ 107 C* ⇌ 62/78 X |
| MDW756 | (structure) | I ⇌ 158 A ⇌ 149 C* ⇌ 80/98 X |
| MDW652 | (structure) | I ⇌ 79 C* ⇌ 34/68 X |
| MDW661 | (structure) | I ⇌ 138 A ⇌ 85/107 X |
| MDW686 | (structure) | I ⇌ 116 C* ⇌ 106/126 X |
| MDW747 | (structure) | I ⇌ 130.5 A ⇌ 149 C ⇌ 89 Sx ⇌ 87 X |
| MDW760 | (structure) | I ⇌ 97 N ⇌ 95/115 X |
| MDW746 | (structure) | I ⇌ 71/93 X |

TABLE 7-continued

| ID# | Structure | Mesomorphic Properties |
|---|---|---|
| MDW662 | $C_6H_{13}O$-phenyl-CH=CH-pyrimidine-(2,3-diF-phenyl)-O-CH$_2$-C*(CH$_3$)(F)-C$_5H_{11}$ | I $\xrightarrow{152}$ A $\xrightarrow{102}$ C $\underset{94}{\overset{52}{\rightleftarrows}}$ X |

TABLE 8

| Chiral Dopant | Phase Diagram of dopant at 10% conc. in MX6111 | Ps (nC/cm$^2$) | τ10–90 (5V/μm) | Tilt angle (θ) |
|---|---|---|---|---|
| MDW 656 | I $\xleftrightarrow{81}$ N $\xleftrightarrow{77}$ A $\xleftrightarrow{65}$ C* | −5.4 | 131 | 22 |
| MDW 658 | I $\xleftrightarrow{79}$ N $\xleftrightarrow{76}$ A $\xleftrightarrow{63}$ C* | −6.5 | 115 | 21 |
| MDW 659 | I $\xleftrightarrow{79}$ N $\xleftrightarrow{77}$ A $\xleftrightarrow{62}$ C* | −3.5 | 215 | 22 |
| MDW 663 | I $\xleftrightarrow{80}$ N $\xleftrightarrow{72}$ A $\xleftrightarrow{67}$ C* | −3.9 | 225 | 24 |
| MDW 665 | I $\xleftrightarrow{81}$ N $\xleftrightarrow{76}$ A $\xleftrightarrow{67}$ C* | −4.7 | 170 | 23 |
| MDW 666 | I $\xleftrightarrow{80}$ N $\xleftrightarrow{73}$ A $\xleftrightarrow{67}$ C* | −6.4 | 185 | 25 |
| MDW 607 | I $\xleftrightarrow{80}$ N $\xleftrightarrow{75}$ A $\xleftrightarrow{67}$ C* | −6.0 | 93 | 24 |
| MDW 624 | I $\xleftrightarrow{82}$ N $\xleftrightarrow{79}$ A $\xleftrightarrow{64}$ C* | −7.6 | 128 | 22 |
| MDW 628 | I $\xleftrightarrow{82}$ N $\xleftrightarrow{75}$ A $\xleftrightarrow{68}$ C* | −6.4 | 115 | 25 |
| MDW 652 | I $\xleftrightarrow{78}$ N $\xleftrightarrow{73}$ A $\xleftrightarrow{65}$ C* | −3.4 | | |
| MDW 661 | I $\xleftrightarrow{80}$ A $\xleftrightarrow{RT}$ C* | —* | | |
| MDW 686 | I $\xleftrightarrow{80}$ N $\xleftrightarrow{75}$ A $\xleftrightarrow{71}$ C* | −8.7 | 117 | 25.5 |
| MDW 756 | I $\xleftrightarrow{79}$ N $\xleftrightarrow{74}$ A $\xleftrightarrow{62}$ C* | −4.89 | 158 | 21 |
| MDW 759 | I $\xleftrightarrow{76}$ N $\xleftrightarrow{70}$ A $\xleftrightarrow{59}$ C* | −5.24 | | |
| MDW 760 | I $\xleftrightarrow{77}$ N $\xleftrightarrow{68}$ A $\xleftrightarrow{59}$ C* | −5.62 | | |
| MDW 746 | I $\xleftrightarrow{74}$ N $\xleftrightarrow{64}$ A $\xleftrightarrow{}$ C* | —* | | |
| MDW 747 | I $\xleftrightarrow{72}$ N $\xleftrightarrow{52}$ A $\xleftrightarrow{}$ C* | —* | | |
| MDW 662 | I $\xleftrightarrow{}$ N $\xleftrightarrow{}$ A $\xleftrightarrow{}$ C* | —* | | |

*polarization less than about 0.4 nc/cm$^2$

TABLE 9

The composition of MX6111 is:

| Short name MX6111 | Structure | (% w/w) |
|---|---|---|
| 706 | 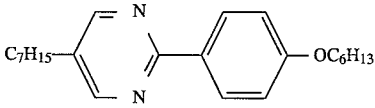 C$_7$H$_{15}$—[pyrimidine]—[phenyl]—OC$_6$H$_{13}$ | 5.6 |
| 707 | C$_7$H$_{15}$—[pyrimidine]—[phenyl]—OC$_7$H$_{15}$ | 5.6 |
| 708 | C$_7$H$_{15}$—[pyrimidine]—[phenyl]—OC$_8$H$_{17}$ | 5.6 |
| 709 | C$_7$H$_{15}$—[pyrimidine]—[phenyl]—OC$_9$H$_{19}$ | 7.2 |
| 906 | C$_9$H$_{19}$—[pyrimidine]—[phenyl]—OC$_6$H$_{13}$ | 9.6 |
| 907 | C$_9$H$_{19}$—[pyrimidine]—[phenyl]—OC$_7$H$_{15}$ | 7.2 |
| 908 | C$_9$H$_{19}$—[pyrimidine]—[phenyl]—OC$_8$H$_{17}$ | 5.6 |
| 909 | C$_9$H$_{19}$—[pyrimidine]—[phenyl]—OC$_9$H$_{19}$ | 33.6 |
| 900H | C$_9$H$_{19}$—[pyrimidine]—[phenyl]—O—CH$_2$—[chiral chain] | 20 |

TABLE 10

Comparison of N* and C* Pitch and $P^{s1}$ in Three Ring FLCs of formula: $R_1-X-Ph_1-Ph_2-Ph_3-R^*$

| MDW ID No. | $R_1X$ | $-Ph_1-Ph_2-Ph_3-$ | $R^{*2}$ | $N^{*3}$ | $C^{*4}$ | $P_s^5$ |
|---|---|---|---|---|---|---|
| 624 | $C_6H_{13}$ | phenyl-pyrazine-phenyl | $OMFC_5H_{11}$ | +6 | −5 | −7.6 |
| 607 | $C_6H_{13}O$ | phenyl-pyrazine-phenyl | $OMFC_5H_{11}$ | +12.5 | −8 | −6 |
| 759 | $C_5H_{11}$-CH=CH-$(CH_2)_2O$ | phenyl-pyrazine-phenyl | $OMFC_5H_{11}$ | +8.5 | −9 | −5.4 |
| 756 | $C_3H_7$-CH=CH-$CH_2O$ | phenyl-pyrazine-phenyl | $OMFC_5H_{11}$ | +23 | −8.5 | −4.9 |
| 628 | $C_6H_{13}O$ | (2-F)phenyl-pyrazine-phenyl | $OMFC_5H_{11}$ | +8 | −5 | −6.4 |
| 760 | $C_5H_{11}$ | phenyl-phenyl-pyrimidine | $OMFC_5H_{11}$ | +3.5 | −5.6 | −2 |
| 652 | $C_8H_{17}$ | phenyl-pyridine-(2,3-F)phenyl | $OMFC_5H_{11}$ | +2.5 | +2 | −3.4 |
| 686 | $C_8H_{17}O$ | (2,3-F)phenyl-pyrazine-phenyl | $OMFC_5H_{11}$ | + Very Long | −7 | −8.7 |
| 662 | $C_6H_{13}O$ | phenyl-pyrimidine-(2,3-F)phenyl | $OMC_6H_{13}$ | + Very Long | −4 | Very Small |
| 790 | $C_6H_{13}$ | phenyl-pyrazine-phenyl | $OFC_6H_{13}$ | No $N^{*6}$ | −18 | −6.6 |
| 791 | $C_6H_{13}O$ | phenyl-pyrazine-phenyl | $OFC_6H_{13}$ | No $N^{*6}$ | −5 | −8.2 |

TABLE 10-continued

Comparison of N* and C* Pitch and $P_S$[1] in Three Ring FLCs of formula: $R_1$—X—$Ph_1$—$Ph_2$—$Ph_3$—R*

| MDW ID No. | $R_1$X | —$Ph_1$—$Ph_2$—$Ph_3$— | R*[2] | N*[3] | C*[4] | $P_S$[5] |
|---|---|---|---|---|---|---|
| 787 | $C_6H_{13}O$ | | $OFC_6H_{13}$ | −2.5 | −3 | −10.2 |
| 786 | $C_6H_{13}O$ | | $OFC_6H_{13}$ | — Very Long | −8 | −3.0 |
| 649[7] | $C_8H_{17}$ | | $ODFC_3H_7$ | −9 | −2 | −16 |
| 655[8] | $C_6H_{13}O$ | | $ODFC_3H_7$ | −37 | −2 | −8 |

[1] Unless otherwise indicated measurements were made in 10% (w/w) mixtures of the indicated dopant in MX 6111 host.
[2] OMF = 2S-fluoro-2-methylalkoxy; OF = 2S-fluoralkoxy; ODF = 2(R), 3(R)-difluoralkoxy.
[3] N* measured at 1°–2° C. above N*-A transition, in μm; very long means longer than detectable by the method employed, here at least about 23 μm.
[4] C* measured at room temperature, in μm.
[5] Measured at about room temperature, in nc/cm$^2$; Note: $P_o = 10 \times P_S/\sin\Theta$ where $\Theta$ = tilt angle; very small means below about 0.4 nc/cm$^2$, the limit of detection of the method employed.
[6] The mixture had no N* phase
[7] 10% (w/w) mixture in MX 6396, data from USSN 08/006,263
[8] 10% (w/w) mixture in MX 6033, data from USSN 08/006,263

TABLE 11

Comparison of N* and C* Pitch and $P_S$[1] in Two Ring FLCs of formula: $R_1$—X—$Ph_1$—$Ph_2$—R*

| MDW ID NO. | $R_1$X | —$Ph_1$—$Ph_2$— | R*[2] | N*[3] | C*[4] | $P_S$[5] |
|---|---|---|---|---|---|---|
| 746 | $C_{10}H_{21}O$ | | $OMFC_5H_{11}$ | NM | NM | very small |
| 747 | $C_8H_{17}O$ | | $OMFC_5H_{11}$ | NM | NM | very small |
| 788 | $C_8H17$ | | $OFC_6H_{13}$ | −7.4 | −5 | −9.3 |
| 789 | $C_{10}H_{21}$ | | $OFC_6H_{13}$ | +13 | +5 | +6.9 |

TABLE 11-continued
Comparison of N* and C* Pitch and $P_S^1$ in Two Ring FLCs of formula: $R_1-X-Ph_1-Ph_2-R*$
| MDW ID NO. | $R_1X$ | $-Ph_1-Ph_2-$ | $R*^2$ | $N*^3$ | $C*^4$ | $P_S^5$ |
|---|---|---|---|---|---|---|
| 792 | $C_{10}H_{21}$ | 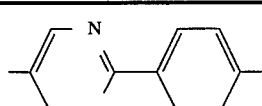 | $OFC_8H_{17}$ | −7 | −1.7 | −7.6 |
| 793 | $C_8H_{17}$ | 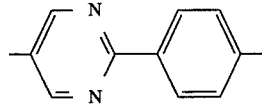 | $OFC_8H_{17}$ | −6 | −4 | −8.9 |
| 794 | $C_{10}H_{21}O$ | 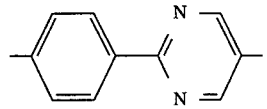 | $OFC_8H_{17}$ | −2.5 | −6 | −4.7 |
| 795 | $C_{10}H_{21}O$ | 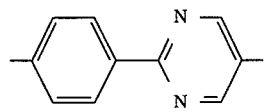 | $OFC_6H_{13}$ | −2.6 | −4 | −5.8 |
| 801 | $C_8H_{17}O$ | 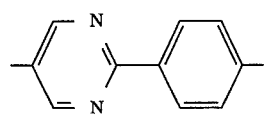 | $OFC_{10}H_{21}$ | −8 | −6.5 | −4.9 |
| 802 | $C_8H_{17}O$ | 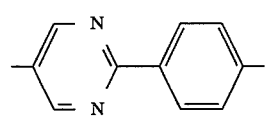 | $OFC_8H_{17}$ | −6 | −4.7 | −4.9 |
| 232[6] | $C_8H_{17}$ | 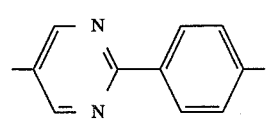 | $ODFC_3H_7$ | −7 | −2 | −23.5 |
| 428[6] | $C_8H_{17}O$ | 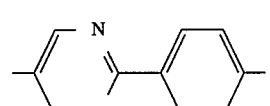 | $ODFC_3H_7$ | −4 | −3 | −13.7 |
| 432[6] | $C_8H_{17}$ | 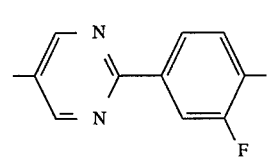 | $ODFC_3H_7$ | +16 | −6 | −15.0 |
| 427[6] | $C_8H_{17}O$ | 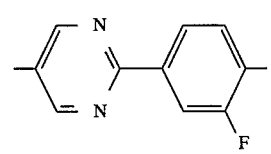 | $ODFC_3H_7$ | −4 | −6 | −8.9 |
| 434[6] | $C_8H_{17}$ | 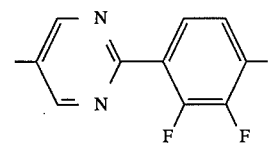 | $ODFC_3H_7$ | +3 | −3 | −18.3 |

TABLE 11-continued

Comparison of N* and C* Pitch and $P_S$[1] in Two Ring FLCs of formula: $R_1-X-Ph_1-Ph_2-R^*$

| MDW ID NO. | $R_1X$ | $-Ph_1-Ph_2-$ | $R^{*2}$ | $N^{*3}$ | $C^{*4}$ | $P_S{}^5$ |
|---|---|---|---|---|---|---|
| 433[6] | $C_8H_{17}$ | 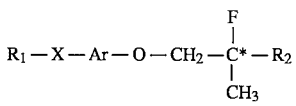 | $ODFC_3H_7$ | +7.1 | −3 | −12.7 |

[1]Unless otherwise indicated, measurements were made in 10% (w/w) mixtures of the indicated dopant in MX 6111 host.
[2]OMF = 2S-fluoro-2-methylalkoxy; OF = 2S-fluoroalkoxy; ODF = 2(R), 3(R)-difluoroalkoxy.
[3]N* measured 1°–2° C. above N* to A transition, in μm.
[4]C* measured at about room temperature, in μm.
[5]Measured at about room temperature in nc/cm²; Note $P_o = 10 \times P_S/\sin\Theta$ in 10% (w/w) mixtures with hosts, where $\Theta$ = tilt angle; very small means below the level of detection in the technique used here less than about 0.4 nc/cm².
[6]10% (w/w) mixtures in MX 6033, data from USSN 08/006,263.

We claim:

1. A ferroelectric liquid crystal composition exhibiting a polarization density and having a smectic phase and a nematic phase in which the nematic phase pitch is opposite in sign to said polarization density which comprises a ferroelectric liquid crystal host material and a chiral nonracemic compound of formula

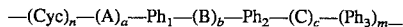

wherein * indicates a chiral carbon, $R_1$ and $R_2$, independently of one another, can be an alkyl, alkenyl or alkynyl group wherein one or more non-neighboring $CH_2$ groups can be replaced with an O, S or a silyl group ($R_A SiR_B$) wherein $R_A$ and $R_B$, independently of one another, are alkyl or alkenyl having from one to six carbon atoms; $R_1$ having from about 3 to about 20 carbon atoms, and $R_2$ having from 1 to about 18 carbon atoms; X is O, S, CO, COO, OCO, COS or a single bond where Ar is a liquid crystal core moiety having two or three aromatic rings of the formula:

$-(Cyc)_n-(A)_a-Ph_1-(B)_b-Ph_2-(C)_c-(Ph_3)_m-$ wherein $Ph_1$, $Ph_2$, and $Ph_3$, independently of one another, are selected from the group consisting of aromatic rings: 1,4-phenyl group, 1,4-phenyl group substituted with 1 or 2 halogens, 1,4-phenyl group wherein one or two of the ring carbons are replaced with nitrogen atoms or a thiadiazole ring; A, B, and C, independently of one another, can be O, S, $CH_2O$, $OCH_2$, $CH_2S$, $SCH_2$, $CH_2OCO$, $CH_2CO_2$, $CH_2CH_2$, COO, OCO, COS, a double or a triple bond; a, b, and c are either 1 or 0 and a+b+c is 2 or less; Cyc is a 1,4-substituted cyclohexyl or a cyclohexenyl ring which can be further substituted with a halogen atom or a cyano group or wherein one or two of the $CH_2$ groups of the ring can be replaced with an oxygen atom; and n and m, independently of one another, are 0 or 1 except that when m=0 then c=0.

2. A ferrolectric liquid crystal composition according to claim 1 wherein in said chiral nonracemic compound a, b, c and n are all zero; m is 1; and $Ph_1$, $Ph_2$ and $Ph_3$, independently of one another, are selected from the group consisting of 1,4-phenyl, 1,4-phenyl substituted with 1 or 2 fluorine atoms, a2,5-pyrimidinyl or a 2,5-pyridinyl group.

3. A ferroelectric liquid crystal composition according to claim 2 in which the smectic C phase pitch is opposite in sign to the nematic phase pitch.

4. A chiral nonracemic compound of formula:

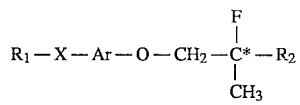

wherein * indicates a chiral carbon, $R_1$ and $R_2$, independently of one another, can be an alkyl, alkenyl or alkynyl group wherein one or more non-neighboring $CH_2$ groups can be replaced with an O, S or a silyl group ($R_A SiR_B$) wherein $R_A$ and $R_B$ independently of one another, are alkyl or alkenyl having from one to six carbon atoms; $R_1$ having from about 3 to about 20 carbon atoms, and $R_2$ having from 1 to about 18 carbon atoms; X is O, S, CO, COO, OCO, COS or a single bond where Ar is a liquid crystal core moiety having two or three aromatic rings of the formula:

$-(Cyc)_n-(A)_a-Ph_1-(B)_b-Ph_2-(C)_c-(Ph_3)_m-$ wherein $Ph_1$, $Ph_2$, and $Ph_3$, independently of one another, are selected from the group consisting of aromatic rings: 1,4-phenyl group, 1,4-phenyl group substituted with 1 or 2 halogens, 1,4-phenyl group wherein one or two of the ring carbons are replaced with nitrogen atoms or a thiadiazole ring;

A, B, and C independently of one another, can be O, S, $CH_2O$, $OCH_2$, $CH_2S$, $SCH_2$, $CH_2OCO$, $CH_2CO_2$, $CH_2CH_2$, COS, COO, OCO, a double or a triple bond; a, b, and c are either 1 or 0 and a+b+c is 2 or less; Cyc is a 1,4-substituted cyclohexyl or a cyclohexenyl ring which can be further substituted with a halogen atom or a cyano group or wherein one or two of the $CH_2$ groups of the ring can be replaced with an oxygen atom; and n and m, independently of one another, are 0 or 1 except that when m is 0 then c is also 0 and except that when B is OCO, n and a are both 0 and m is 1, C cannot be a single bond.

5. A chiral nonracemic compound of formula:

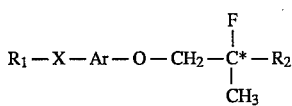

wherein * indicates a chiral carbon, $R_1$ and $R_2$, independently of one another, can be an alkyl, alkenyl or alkynyl group wherein one or more non-neighboring $CH_2$ groups can be replaced with an O, S or a silyl group ($R_A SiR_B$) wherein $R_A$ and $R_B$, independently of one another, are alkyl or alkenyl having from one to six carbon atoms; $R_1$ having from about 3 to about 20 carbon atoms, and $R_2$ having from 1 to about 18 carbon atoms; X is O, S, CO, COO, OCO, COS or a single bond where Ar is a liquid crystal core moiety having two or three aromatic rings of the formula:

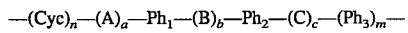

wherein $Ph_1$, $Ph_2$, and $Ph_3$, independently of one another, are selected from the group consisting of aromatic rings: 1,4-phenyl group, 1,4-phenyl group substituted with 1 or 2 halogens, 1,4-phenyl group wherein one or two of the ring carbons are replaced with nitrogen atoms or a thiadiazole ring;

A, B, and C independently of one another, can be O, S, $CH_2O$, $OCH_2$, $CH_2S$, $SCH_2$, $CH_2OCO$, $CH_2CO_2$, $CH_2CH_2$, COS, COO, OCO, a double or a triple bond; a, b, and c are either 1 or 0 and a+b+c is 2 or less; Cyc is a 1,4-substituted cyclohexyl or a cyclohexenyl ring which can be further substituted with a halogen atom or a cyano group or wherein one or two of the $CH_2$ groups of the ring can be replaced with an oxygen atom; and n and m, independently of one another, are 0 or 1 except that when m is 0 then c is also 0 and when one of B or C is COO or OCO, the other of B or C cannot be a single bond.

6. The compound of claim 5 wherein B and C are selected from the group O, S, $CH_2O$, $OCH_2$, $CH_2S$, $SCH_2$, $CH_2OCO$, $CH_2CO_2$, $CH_2CH_2$, COS, a double or a triple bond.

7. The compound of claim 5 where m is 1.

8. The compound of claim 5 wherein one of B or C is a triple bond.

9. The compound of claim 8 wherein the other of B or C is COO or OCO.

10. The compound of claim 5 wherein each of a, b and c is 0.

11. The compound of claim 5 wherein m is 0, c is 0 and B is COO or OCO.

12. The compound of claim 5 wherein B and C are either a triple bond or a single bond.

13. A chiral nonracemic compound of formula:

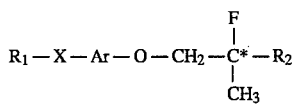

wherein * indicates a chiral carbon, $R_1$ and $R_2$, independently of one another, can be an alkyl, alkenyl or alkynyl group wherein one or more non-neighboring $CH_2$ groups can be replaced with an O, S or a silyl group ($R_A SiR_B$) wherein $R_A$ and $R_B$, independently of one another, are alkyl or alkenyl having from one to six carbon atoms; $R_1$ having from about 3 to about 20 carbon atoms, and $R_2$ having from 1 to about 18 carbon atoms; X is O, S, CO, COO, OCO, COS or a single bond where Ar is a liquid crystal core moiety having two or three aromatic rings of the formula:

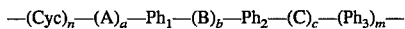

wherein $Ph_1$, $Ph_2$, and $Ph_3$, independently of one another, are selected from the group consisting of aromatic rings: 1,4-phenyl group, 1,4-phenyl group substituted with 1 or 2 halogens, 1,4-phenyl group wherein one or two of the ring carbons are replaced with nitrogen atoms or a thiadiazole ring;

A, B, and C independently of one another, can be O,S, $CH_2O$, $OCH_2$, $CH_2S$, $SCH_2$, $CH_2OCO$, $CH_2CO_2$, $CH_2CH_2$, COO, OCO, COS, a double or a triple bond; a, b, and c are either 1 or 0 and a+b+c is 2 or less; Cyc is a 1,4-substituted cyclohexyl or a cyclohexenyl ring which can be further substituted with a halogen atom or a cyano group or wherein one or two of the $CH_2$ groups of the ring can be replaced with an oxygen atom; and where m is 0 or 1 and n is 1 except that when m =0 then c=0.

14. The compound of claim 13 said core Ar comprises a transcyclohexane or transcyclohexene ring.

15. The compound of claim 13 wherein A, if present, is $CH_2O$.

16. The compound of claim 13 wherein X is O, S or a single bond; A, if present, is $CH_2O$ and B and C independently of one another, are selected from COO, OOC or a triple bond.

17. The compound of claim 13 wherein X is O, S or a single bond; A, if present, is $CH_2CH_2$ and B and C independently of one another, are selected from COO, OOC or a triple bond.

18. The compound of claim 13 wherein in said core b, c are all 0; and m=1.

19. The compound of claim 13 wherein said halogen substituted 1,4-phenyl group is substituted with fluorine.

20. The compound of claim 19 wherein said fluorine substituted 1,4-phenyl group is substituted in the ortho position, the meta position or both.

21. The compound of claim 13 wherein $R_1$ is an alkyl or alkoxy group having from about 3–12 carbon atoms and $R_2$ is an alkyl or alkene having from about 2 to about 12 carbon atoms.

22. A chiral nonracemic compound of formula:

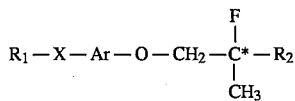

wherein * indicates a chiral carbon, $R_1$ and $R_2$, independently of one another, can be an alkyl, alkenyl or alkynyl group wherein one or more non-neighboring $CH_2$ groups can be replaced with an O, S or a silyl group ($R_A SiR_B$) wherein $R_A$ and $R_B$, independently of one another, are alkyl or alkenyl having from one to six carbon atoms; $R_1$ having from about 3 to about 20 carbon atoms, and $R_2$ having from 1 to about 18 carbon atoms; X is O, S, CO, COO, OCO, COS or a single bond where Ar is a liquid crystal core moiety having two or three aromatic rings of the formula:

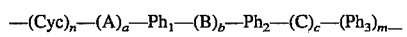

wherein

Ph₁, Ph₂, and Ph₃, independently of one another, are selected from the group consisting of aromatic rings: 1,4-phenyl group, 1,4-phenyl group substituted with 1 or 2 halogens, 1,4-phenyl group wherein one or two of the ring carbons are replaced with nitrogen atoms or a thiadiazole ring;

except that at least one of Ph₁, Ph₂ or Ph₃ is a 1,4-phenyl group wherein one or two of the ring carbons are replaced with nitrogen rings;

A, B, and C independently of one another, can be O, S, $CH_2O$, $OCH_2$, $CH_2S$, $SCH_2$, $CH_2OCO$, $CH_2CO_2$, $CH_2CH_2$, COO, OCO, COS, a double or a triple bond; a, b, and c are either 1 or 0 and a+b+c is 2 or less; Cyc is a 1,4-substituted cyclohexyl or a cyclohexenyl ring which can be further substituted with a halogen atom or a cyano group or wherein one or two of the $CH_2$ groups of the ring can be replaced with an oxygen atom; and n and m, independently of one another, are 0 or 1 except that when m=0 then c=0.

23. The compound of claim 22 wherein X is O, S, or a single bond; and B and C independently of one another and if present, are selected from COO, OOC or a triple bond.

24. The compound of claim 22 wherein X is O, S or a single bond and B and C independently of one another and if present, are triple bonds.

25. The compound of claim 22 wherein X is O or a single bond; A is $CH_2O$ or $CH_2$—$CH_2$; and a, b, and c are all 0.

26. The compound of claim 22 wherein in said core a, b, c and n are all 0 and m is 1.

27. The compound of claim 22 wherein Ph₁, Ph₂ and Ph₃, independently of one another, are selected from the group 1,4-phenyl, 1,4-phenyl substituted with 1 or 2 fluorine atoms, a 2,5-pyrimidinyl or a 2,5-pyridinyl group.

28. The compound of claim 22 wherein a, b, c, m and n are all zero and wherein Ph₂ and Ph₂, independently of one another, are selected from the group 1,4-phenyl, 1,4-phenyl substituted with 1 or 2 fluorine atoms, a 2,5-pyrimidinyl or a 2,5-pyridinyl group.

29. The compound of claim 22 wherein n is 1; A, if present, is $CH_2O$ or $CH_2CH_2$; and said core Ar comprises a transcyclohexane or transcyclohexene ring.

30. The compound of claim 22 wherein the core Ar is

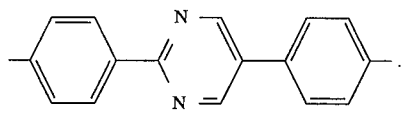

31. The compound of claim 22 wherein the core Ar is

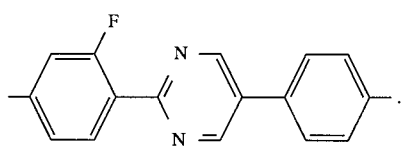

32. The compound of claim 22 wherein the core Ar is

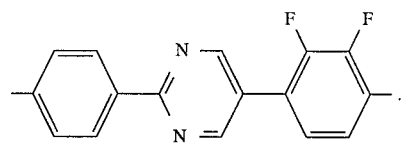

33. The compound of claim 22 wherein the core Ar is

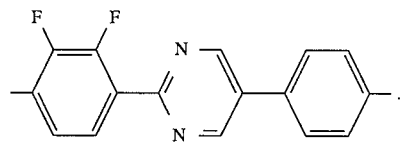

34. The compound of claim 22 wherein the core Ar is

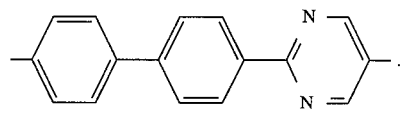

35. The compound of claim 22 wherein Ar is selected from the cores:

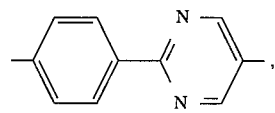,

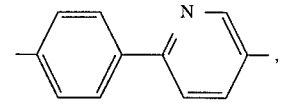,

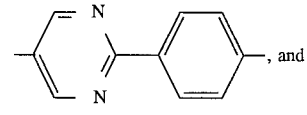, and

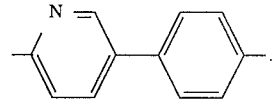.

36. The compound of claim 22 wherein $R_1$ is an alkyl or alkoxy group having from about 3 to about 12 carbon atoms and $R_2$ is an alkyl or alkene group having from 2 to about 12 carbon atoms.

37. The compound of claim 22 wherein at least one of Ph₁, Ph₂ or Ph₃ is a 1,4-phenyl group wherein one or two of the ring carbons are replaced with nitrogen rings.

38. The compound of claim 22 where m is 1.

39. The compound of claim 22 wherein Ph₁, Ph₂ and Ph₃, independently of one another, are selected from the group 1,4-phenyl, 1,4-phenyl substituted with 1 or 2 fluorine atoms, a 2,5-pyrimidinyl or a 2,5-pyridinyl group.

40. The compound of claim 22 wherein Ph₁, Ph₂ and Ph₁, independently of one another, are selected from the group 1,4-phenyl, 1,4-phenyl substituted with 1 or 2 fluorine atoms, a 2,5-pyrimidinyl or a 2,5-pyridinyl group.

41. The compound of claim 22 wherein $R_1$ is an alkyl or alkoxy group having from about 3 to about 12 carbon atoms and $R_2$ is an alkyl or alkene group having from 2 to about 12 carbon atoms.

42. A chiral nonracemic compound of claim 5 which when added to an achiral liquid crystal mixture having a smectic phase and a nematic phase imparts to the resulting chiral nonracemic mixture a nematic phase pitch that is opposite in sign to the polarization density of said resulting admixture.

43. A chiral nonracemic compound of claim 13 which when added to an achiral liquid crystal mixture having a smectic phase and a nematic phase imparts to the resulting chiral nonracemic mixture a nematic phase pitch that is opposite in sign to the polarization density of said resulting admixture.

44. A chiral nonracemic compound of claim 22 which when added to an achiral liquid crystal mixture having a smectic phase and a nematic phase imparts to the resulting chiral nonracemic mixture a nematic phase pitch that is opposite in sign to the polarization density of said resulting admixture.

45. A chiral nonracemic compound of claim 42 which also imparts smectic C pitch to said admixture which is opposite in sign to the nematic pitch of said admixture.

46. A chiral nonracemic compound of claim 5 which is a pitch compensation agent.

* * * * *

UNITED STATES PATENT AND TRADEMARK OFFICE
CERTIFICATE OF CORRECTION

PATENT NO. : 5,453,218                                Page 1 of 2
DATED : September 26, 1995
INVENTOR(S) : Wand et al It is certified that error appears in the above-indentified patent and that said Letters Patent is hereby corrected as shown below:

In Tables 1, 2, and 3, in the heading and body of the Tables, and in Tables 4, 5, and 6, in the body of the Tables, please rewrite all labels of the exemplary core with the Arabic numeral --1-- in place of Roman numeral "I".

In Table 5 in the heading, please insert the explanatory label --$R_1$-X-$Ph_1$-B-$Ph_2$-C-$Ph_3$-$R^*$ If'--.

In Table 6, in the heading of both column 25 and 26, in the explanatory formulas, "$R_1$X-Cyc-$(A)_a$-$Ph_1$-$Ph_2$ - - $R^*$" should be rewritten as --$R_1$X-Cyc-$(A)_a$-$Ph_1$-$Ph_2$ - $R^*$--, and formula "$R_1$X-Cyc-$CH_2$O-$Ph_1$--$Ph_2$-$R^*$" should be rewritten as --$R_1$X-Cyc-$CH_2$O-$Ph_1$-$Ph_2$-$R^*$--. The extra "-" should be deleted.

UNITED STATES PATENT AND TRADEMARK OFFICE
CERTIFICATE OF CORRECTION

PATENT NO. : 5,453,218
DATED : September 26, 1995
INVENTOR(S) : Wand et al

It is certified that error appears in the above-indentified patent and that said Letters Patent is hereby corrected as shown below:

In Table 10, in the heading of both columns 33 and 34, and 35 and 36, the formula "$R_1-X-Ph_1-Ph_2-Ph_3-R^*$" should be written on one line, not on two lines.

In Table 10, column 34, the first row in the Table, the entry under $C^*$, "-5" should be rewritten as --4--.

In Table 10, column 35, in the footnote 2 to the Table, "2S-fluoralkoxy" should be rewritten as --2S-fluoroalkoxy-- and in footnote 5, "$P_o=10 \times P_s/\sin\theta$" should be rewritten as --$P_o=10 \times P_s/\sin\theta$--

Signed and Sealed this

Twenty-third Day of July, 1996

Attest:

BRUCE LEHMAN

*Attesting Officer*  *Commissioner of Patents and Trademarks*